US00PP14780P2

(12) United States Plant Patent
Fear et al.

(10) Patent No.: US PP14,780 P2
(45) Date of Patent: May 11, 2004

(54) BLACKBERRY PLANT NAMED 'DRISCOLL COWLES'

(50) Latin Name: *Rubus L.* subgenus *Rubus*
Varietal Denomination: Driscoll Cowles

(75) Inventors: Carlos D. Fear, Aptos, CA (US); Gavin Sills, Watsonville, CA (US); Fred M. Cook, Aptos, CA (US); Richard E. Harrison, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/306,457

(22) Filed: Nov. 27, 2002

(51) Int. Cl.[7] ..... A01H 5/00
(52) U.S. Cl. ..... Plt./203
(58) Field of Search ..... Plt./203, 204

*Primary Examiner*—Anne Marie Grunberg
*Assistant Examiner*—Susan B. McCormick
(74) *Attorney, Agent, or Firm*—Pennie & Edmonds LLP

(57) ABSTRACT

The present invention relates to a new and distinct cultivar of blackberry plant named Driscoll Cowles. The new cultivar is distinguished from other blackberry cultivars by its mid-late season crop, large fruit size and thornless canes. Driscoll Cowles produces fruit with improved quality and shipping characteristics. The new cultivar is distinguished from its seed parent by having larger fruit; it is distinguished from its pollen parent by its larger, better flavored fruit.

2 Drawing Sheets

1. BACKGROUND OF THE INVENTION

This invention relates to a new cultivar of blackberry called 'Driscoll Cowles'. The new cultivar was developed from hybridization of the female cultivar 'Sonoma' (U.S. patent application Ser. No. 09/772,330) with the unpatented male variety 'Loch Ness'. The parents were crossed in 1993 where after fruit and seed were collected to produce seedlings for field planting in Watsonville, Calif. in 1994. The new cultivar was selected in 1995 for its good flavor, large fruit size, fruit firmness and thornless canes. The cultivar has been asexually propagated in Watsonville, Calif. and reproduced true to type plants by in vitro shoot tip culture.

1.1 Latin name of the genus and species of the plant claimed: The variety is botanically identified as *Rubus L.* subgenus *Rubus.*

2. SUMMARY OF THE INVENTION

The present invention provides a new and distinct blackberry cultivar named 'Driscoll Cowles'. The variety is botanically identified as *Rubus L.* subgenus *Rubus.* The variety is a complex Rubus hybrid, which can be characterized as an erect tetraploid with considerable *R. alleghenien-sis* background with other species such as *R. trivialis, R. argutus R. procerus,* and *R. ulmifolious* also appearing in its background. The new cultivar produces a floricane crop which begins in mid-July and continues until late September. The new blackberry variety is distinguished from other varieties by a number of characteristics as set forth in Table 1. In particular, the new cultivar is distinguished by its mid-late season of fruit ripening, its large fruit size and its improved flavor.

3. COMPARISON TO SIMILAR VARIETIES

The variety that we believe to be similar to 'Driscoll Cowles' from those known to us is 'Chester', an unpatented variety. 'Driscoll Cowles' is particularly different from 'Olallie' by being slightly earlier ripening, having larger fruit size and having less acidic flavor. Further detailed comparison of 'Driscoll Cowles' to 'Olallie' and 'Chester' is presented in Table1.

4. BRIEF DESCRIPTION OF THE DRAWINGS

The accompanying photographs show typical specimens of the fruit, leaves and shoot of the new cultivar, in color as nearly true as reasonably possible in color illustrations of this type.

Figure 1:
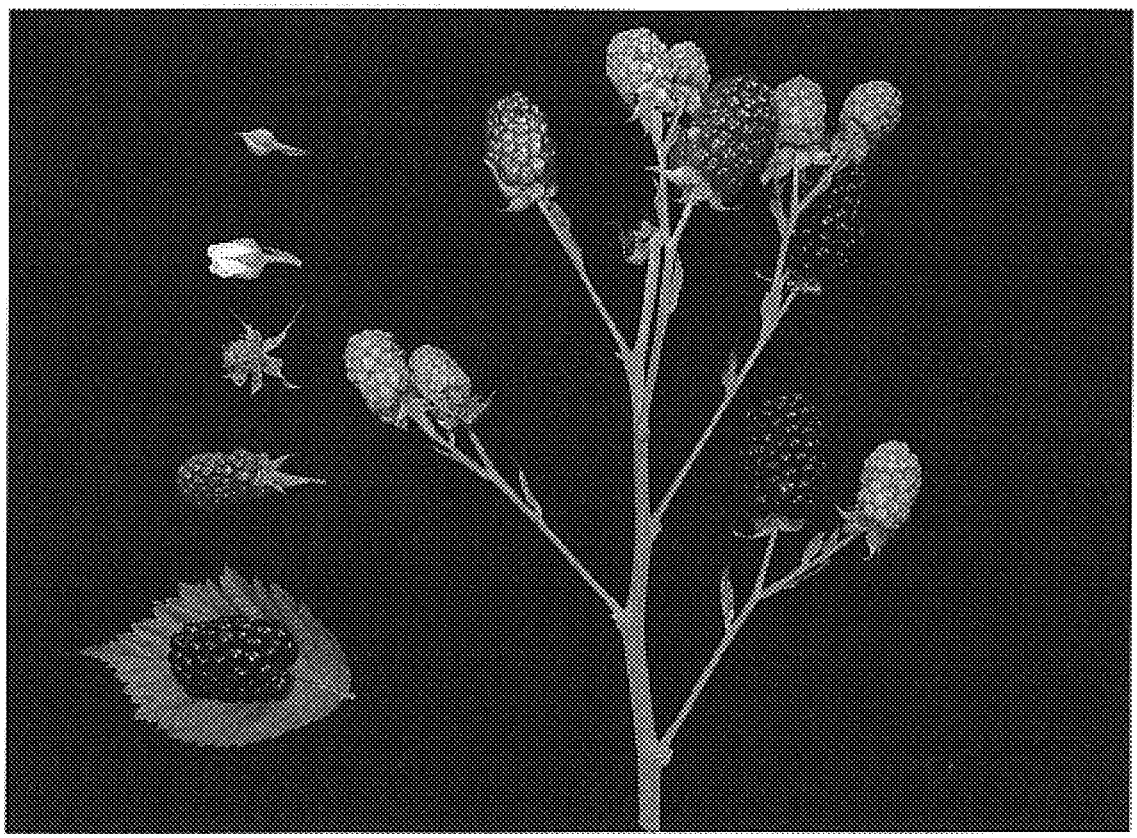

FIG. 1. is a photograph of a 'Driscoll Cowles' fruiting lateral branch with fruit in various stages of development.

Figure 2:
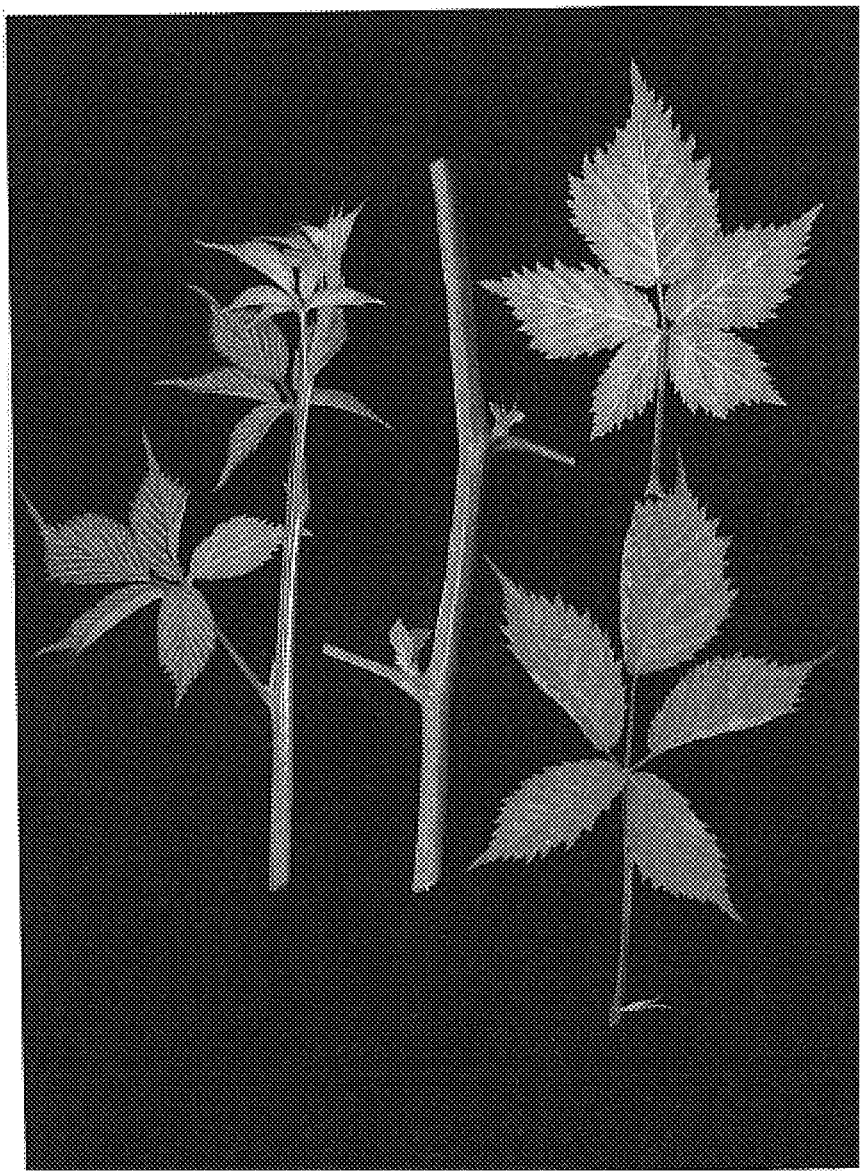

FIG. 2. is a photograph showing a close-up view of a primocane shoot, mature leaf and stem of 'Driscoll Cowles'.

5. DESCRIPTION OF THE NEW VARIETY

The following detailed description of the new blackberry cultivar, 'Driscoll Cowles', is based upon recorded observations of 2–5 year old plants and fruit grown between 1998 and 2002 in Watsonville, Calif., and is believed to apply to plants of the 'Driscoll Cowles' cultivar grown in similar conditions of soil and climate elsewhere. Plants were planted on soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data with a capital letter and an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

5.1 CHARACTERISTICS OF THE NEW VARIETY

Table 1 provides information on the plant and fruit characteristics of the new blackberry cultivar 'Driscoll Cowles' compared with characteristics of the unpatented blackberry cultivars 'Olallie' and 'Chester'. Both 'Olallie' and 'Chester' are currently important cultivars for fresh market shipping, and thus are comparable to the proposed use of the new invention, 'Driscoll Cowles'. Observations of 'Driscoll Cowles', 'Olallie' and 'Chester' were taken in side-by-side comparison between 1998 and 2002.

Fruit of the new cultivar is particularly characterized and distinguished from other cultivars by its improved flavor, larger size, and thornless canes.

'Driscoll Cowles' is moderately productive and produces most of its crop in the mid to late part of the harvest season. Canes of 'Driscoll Cowles' are vigorous, thornless and have buds with a moderate to high chill requirement. The average plant height is about 334 cm and the average plant spread is about 85 cm. The pigmentation of the young shoots is 145A. The sepals average about 9.9 mm in length and the average width of a sepal is about 4.9 mm. Sepal pigmentation color is 146B. The coloration of the pedicel is 144A.

The style pigmentation color is 143B, the average number of styles per flower is about 121, the anther pigmentation color is 155A, and the average number of anthers per flower is about 180. The number of petals per flower is five. The color of the seeds of 'Driscoll Cowles' is 152A and the average seed weight is 3.3 mg.

'Driscoll Cowles' is distinguished from its pollen parent, 'Loch Ness', by having larger better flavored fruit. 'Driscoll Cowles' is distinguished from its seed parent, 'Sonoma', by having larger fruit.

TABLE 1

PLANT CHARACTERISTICS OF 'DRISCOLL COWLES'

| | Driscoll Cowles | Chester | Olallie |
|---|---|---|---|
| GENERAL | | | |
| Vigor | high | high | moderate-high |
| Growth habit | semi-erect | semi-erect | spreading |
| Productivity | moderate | high | high |
| Self-fruitfulness | self-fruitful | self-fruitful | self-fruitful |
| Time of bud burst | late | late | early |
| CANES | | | |
| Primocanes | | | |
| Young shoot pigmentation | medium | medium | weak |
| Glucosity (waxy bloom) | absent weak | medium | weak |
| Cane cross section from mid) cane of primocane) | grooved | angular to grooved | rounded to angular |
| Dormant cane color | purple brown | purple brown | brown to purple brown |
| Spines | absent | absent | present |
| Pubescence on canes | present | present | present |
| LEAVES | | | |
| Length (cm) | 8.9 | 9.2 | 8.4 |
| Width (cm) | 5.6 | 6.4 | 6.3 |
| Relief between veins | strong | weak | medium |
| Number of leaflets | usually 5 | usually 5 | sometimes 3, sometimes 5 |
| Glossiness | medium | medium | medium |

TABLE 1-continued

PLANT CHARACTERISTICS OF 'DRISCOLL COWLES'

| | Driscoll Cowles | Chester | Olallie |
|---|---|---|---|
| Cross Section | concave to flat | concave to flat | concave |
| Terminal leaflet | | | |
| Length (cm) | 10 | 10.7 | 9.1 |
| Width (cm) | 7.5 | 8.3 | 7.9 |
| Shape | ovate | ovate | ovate |
| Tip | acuminate | acuminate | acuminate |
| Base | cordate | cordate | cordate |
| Margin | doubly serrated | doubly serrated | doubly serrated |
| Lateral Leaflet | | | |
| Length (cm) | 8.9 | 9.2 | 8.4 |
| Width (cm) | 5.6 | 6.4 | 6.3 |
| Overlap of lateral leaflets | yes | yes | yes |
| Shape | ovate | ovate | ovate |
| Tip | acuminate | acuminate | acuminates |
| Base | rounded to cordate | rounded | rounded |
| Margin | doubly serrate | doubly serrated | doubly serrated |
| Rachis length (between terminal leaflet and adjacent lateral (leaflets) (cm) | 3.8 | 3.0 | 2.5 |
| Overlapping of lateral leaflets | touching | overlapping | overlapping |
| Petiole | | | |
| Length (cm) | 8.6 | 5.9 | 3.9 |
| Pigmentation of upper surface | red purple/ maroon 183B | red purple/ maroon | green to slightly pink |
| Pigmentation of underside | 146A | yellow green | yellow green |
| Stipule orientation | erect | erect | clasping to erect |
| Color | | | |
| Face | 147A | 146A | 146A |
| Underside | 146A | 146A | 146A |
| FLOWERS | | | |
| Flowering period time of beginning of flowering | very late | very late | early |
| Flower size | medium | medium | medium |
| Flower diameters (cm) | 4.7 | 4.3 | 4.3 |
| Flower number (at 3rd node from tip of lateral mean and range) | 7.0 | 9.5 | 4.2 |
| Petal | | | |
| Length (cm) | 2.2 | 2.0 | 2.0 |
| Width (cm) | 1.7 | 1.4 | 1.3 |
| Color | 155-D | N74D | |
| Pedicel | | | |
| Coloration | medium | weak | very weak |
| Length (cm) | 3.5 | 1.8 | |
| FRUIT | | | |
| Fruit harvest season | mid-late | late | early |
| Color | black | black | black |
| Immature | 187-A | 187-A | 187-B |
| Maturing | 202-A | 202-A | 202-A |
| Mature fruit | 202-A | 202-A | 202-A |
| Glossiness | strong | medium | medium |
| Shape | narrow ovate | round to ovate | narrow ovate |

TABLE 1-continued

| PLANT CHARACTERISTICS OF 'DRISCOLL COWLES' | | | |
|---|---|---|---|
| | Driscoll Cowles | Chester | Olallie |
| | to long conical | | |
| Dimensions | | | |
| Fruit size | large | small | medium |
| Length (cm) | 2.9 | 2.1 | 2.9 |
| Width (cm) | 2.2 | 2.0 | 1.7 |
| Weight (g/fruit) | 6.1 | 3.9 | 5.3 |
| Soluble solids (%) | 11.2 | 9.6 | 10.4 |
| Titratable acidity (% as citric acid) | 1.34 | 1.84 | 2.06 |
| Number of druplets/ fruit | 82 | 46 | 86 |
| Firmness | Firm | Firm | Soft |

5.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of 'Driscoll Cowles', 'Chester', and 'Olallie' yielded DNA fragment patterns that uniquely distinguish each of these genetically distinct genotypes.

We claim:

1. A new and distinctive cultivar of blackberry plant, substantially as shown and described.

* * * * *